US005637088A

United States Patent [19]
Wenner et al.

[11] Patent Number: 5,637,088
[45] Date of Patent: Jun. 10, 1997

[54] SYSTEM FOR PREVENTING NEEDLE DISPLACEMENT IN SUBCUTANEOUS VENOUS ACCESS PORTS

[76] Inventors: Donald E. Wenner, 3600 Kessler Pl.; George L. Scott, III, 100 N. Pennsylvania, both of Roswell, N.M. 88201

[21] Appl. No.: 528,319

[22] Filed: Sep. 14, 1995

[51] Int. Cl.6 .................................................. A61M 11/00
[52] U.S. Cl. ............................................. 604/93; 604/175
[58] Field of Search ............................ 604/93, 167, 175, 604/264, 256, 280, 283

[56] References Cited

U.S. PATENT DOCUMENTS

| 4,578,063 | 3/1986 | Inman et al. | 604/175 |
| 4,670,008 | 6/1987 | Von Albertini | 604/165 |
| 4,861,341 | 8/1989 | Woodbum | 604/175 |
| 4,969,870 | 11/1990 | Kramer et al. | 604/51 |
| 5,180,365 | 1/1993 | Ensminger et al. | 604/93 |
| 5,257,973 | 11/1993 | Villasuso | 604/49 |
| 5,312,337 | 5/1994 | Flaherty et al. | 604/93 |
| 5,352,204 | 10/1994 | Ensminger | 604/93 |
| 5,487,739 | 1/1996 | Aebischer et al. | 604/93 |
| 5,527,307 | 6/1996 | Srisathapat et al. | 604/93 X |

*Primary Examiner*—John D. Yasko
*Attorney, Agent, or Firm*—Louis J. Hoffman

[57] ABSTRACT

A threaded, dual needle system is securely attached to a modified subcutaneous venous access port having an internal reservoir, used for intravenous drug therapy particularly in human cancer treatment. A hollow outer needle is paired with a removable, male-threaded solid inner point and inserted through the patient's tissue and through the port's protective, self-sealing silicon septum, and the solid inner needle is then removed, while the outer needle is left in place. Next, a hollow inner needle is threaded through the outer needle to a depth sufficient to interlock with a female-threaded port receptacle at the base of the port's fluid reservoir and rotated to install. Optional additional threading can permit securing the outer needle to the two inner needles. A breakaway system prevents displacement from unintended pulling of the flow-line. The system thus provides additional protection against needle displacement from venous access ports, the resulting leakage, and the problems caused thereby.

20 Claims, 4 Drawing Sheets

SYSTEM FOR PREVENTING NEEDLE DISPLACEMENT IN SUBCUTANEOUS VENOUS ACCESS PORTS

FIELD OF THE INVENTION

The invention is in the field of subcutaneous venous access port devices, which provide for intravenous drug therapy, particularly useful for cancer treatment in humans. The disclosed device is useful in preventing subcutaneous infiltration of chemicals and the resultant toxicity and necrosis of tissues caused by needle displacement in such ports.

BACKGROUND OF THE INVENTION

In existing medical practice, percutaneous catheters are used for intravenous drug therapy. Problems associated with such systems, which multiply when used on a repetitive basis, include substantial sterile dressing care requirements for patients, increased rate of transcutaneous infection, and venous thrombosis. Without a venous access device, there exists significant risk of the development of thrombosis, venous sclerosis, or destruction of smaller peripheral vessels from repeated vein punctures.

Known subcutaneous venous access devices or ports provide numerous advantages for repeated or sustained injection therapy, in comparison to percutaneous catheters. Such ports are surgically installed under the patient's skin for intermittent or continuous intravenous injections, and are often the method of choice for sustained intravenous treatments. However, known needle-port systems have limitations when a treatment regimen includes the use of toxic chemotherapeutic agents, because of the significant potential for needle displacement from the port's protective, self-sealing silicon septum.

Port-needle displacement is hazardous and typically results in subcutaneous diffusion of injected toxic chemicals, causing necrosis of nearby tissues. Needle displacement may also result in poor deployment of the chemical treatment, in addition to causing physical and emotional discomfort to the patient. Necrosis of tissue typically requires corrective surgery, including debridement of the necrotic tissue, removal of the port, and often skin grafting to facilitate healing. Existing subcutaneous venous access ports thus may increase the potential for infections due to needle displacement and toxic chemical infusions, which is particularly hazardous for malnourished or neutropenic patients or patients with suppressed immune systems.

Another potential problem associated with presently available drug infusion devices is associated with the occurrence of thrombosis, which may require a chemical cleaning treatment, or even premature surgical removal for remedial purposes.

A variety of known ports are described in references, such as U.S. Pat. No. 4,861,341, to address needle displacement, however, none adequately controls the problem. For instance, one configuration disclosed in that patent shows a needle core, or stylet, that creates an expansion section that expands upon removal of the stylet. A second embodiment employs a balloon segment of the needle that is manually inflated after placing the needle in the fluid reservoir chamber of the port. Other embodiments provide permanent, multi-ridged surfaces that cooperate with the septum to secure the needle. None of those or other known techniques for securing the needle in the port operate satisfactorily to secure the needle well, and thus are presently not widely used in medical practice.

SUMMARY OF THE INVENTION

It is therefore an object of the present invention to provide a safer system of providing repeated intravenous drug therapy.

It is another object of the invention to provide a venous access port useful in preventing subcutaneous infiltration of chemicals.

It is another object of the invention to reduce the probability of needle displacement from venous access ports.

It is another object of the invention to reduce toxicity and necrosis of tissues caused by needle displacement from venous access ports.

It is another object of the invention to reduce the likelihood of thrombosis caused by needle displacement from venous access ports.

It is another object of the invention to provide a venous access port having an improved dual-needle system.

It is another object of the invention to prevent needle displacement from excessive or unintended pulling on the flow-line to a venous access port.

It is another object of the invention to provide a breakaway section in the flow-line to a venous access port, having a ball valve to prevent discharge of drugs or bodily fluids.

The inventive apparatus and method achieves those and other objects of the invention by the use of a securely attached, threaded, dual needle system in conjunction with a modified subcutaneous port. An embodiment of the invention, illustrated in the drawings, comprises a hollow outer needle having a smooth exterior and internal threading, which is designed to interlock with a removable, oppositely threaded solid inner point, which in one embodiment includes small cutting blades located above the pointed tip. After the outer needle with interlocked solid internal needle is inserted as a unit through the patient's tissue and through the port's protective silicon septum, the solid inner needle is unscrewed and removed, while the outer needle is left in place. Next, a hollow inner needle is inserted through the outer needle to a depth sufficient to interlock with a female-threaded port receptacle at the base of the port's fluid reservoir, and the inner needle is rotated to install. In the disclosed embodiment, the inner hollow needle has an external threaded interval meshing with the outer needle's internal threading, so that the two needles are held together as well as connected to the port. A breakaway section can be placed in the flow-line to the port, to prevent needle displacement from pulling on the flow-line. A ball valve can be used to prevent discharge of drugs or blood if the breakaway section is pulled apart.

The inventive system thus provides additional security against needle displacement from venous access ports, the resulting leakage, and the problems caused thereby. This innovative system offers a safer standard of care and augments the overall efficiency of present port systems, by eliminating or substantially reducing the risk of needle displacement and the resultant medical liabilities.

Additional benefits and advantages of the present invention will be apparent to those skilled in the art to which this invention relates from the following description of the preferred embodiments and claims, in conjunction with the accompanying illustrations.

BRIEF DESCRIPTION OF THE DRAWINGS

The novel features of the invention are described with particularity in the claims. The invention, together with its objects and advantages, will be better understood after referring to the following description and the accompanying figures, in which common numerals are intended to refer to common elements.

DETAILED DESCRIPTION OF PREFERRED EMBODIMENTS

Figure 1:
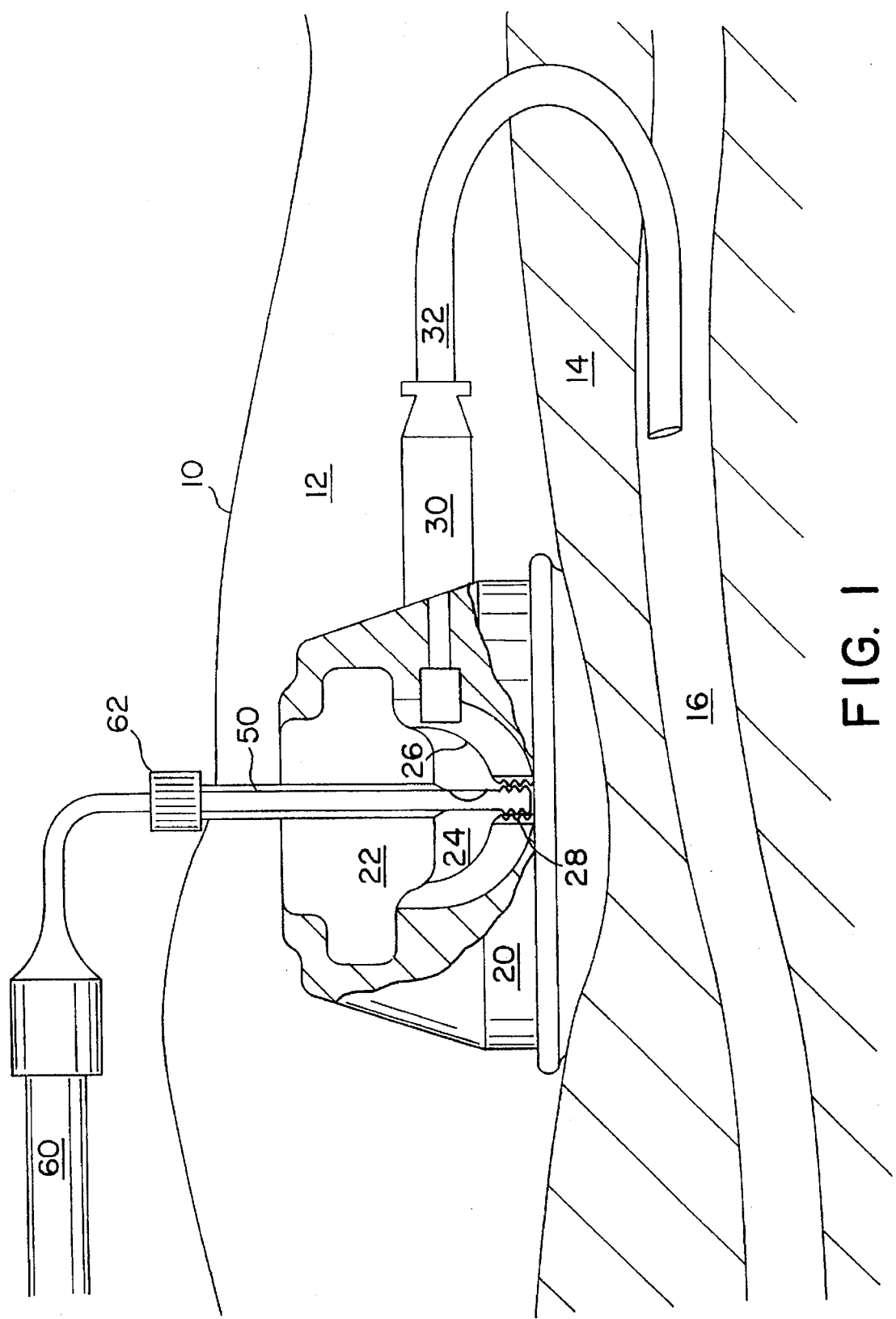
FIG. 1 shows a cut-away view of a subcutaneous venous access port in accordance with the system of the invention.

FIG. 1 depicts a cut-away view of a patient's skin having surface 10, subcutaneous zone 12, deep fascia tissue 14, and vein 16. A subcutaneous venous access port has body 20, silicon septum 22, and fluid storage reservoir 24. Reservoir 24 is connected to the patient's vein, through coupling 30 and catheter 32, which are surgically implanted before or as the port is installed. Such ports, or variations of it, are commercially available to the medical industry. In accordance with the invention, port body 20 has a sloping inner surface 26 adjacent to reservoir 24 and a female-threaded receptacle 28, which is designed to interlock with the threaded needle shown in FIG. 3, as more fully described below. The sloping surface 26 is concave, as observed from inside reservoir 24.

Figure 2:
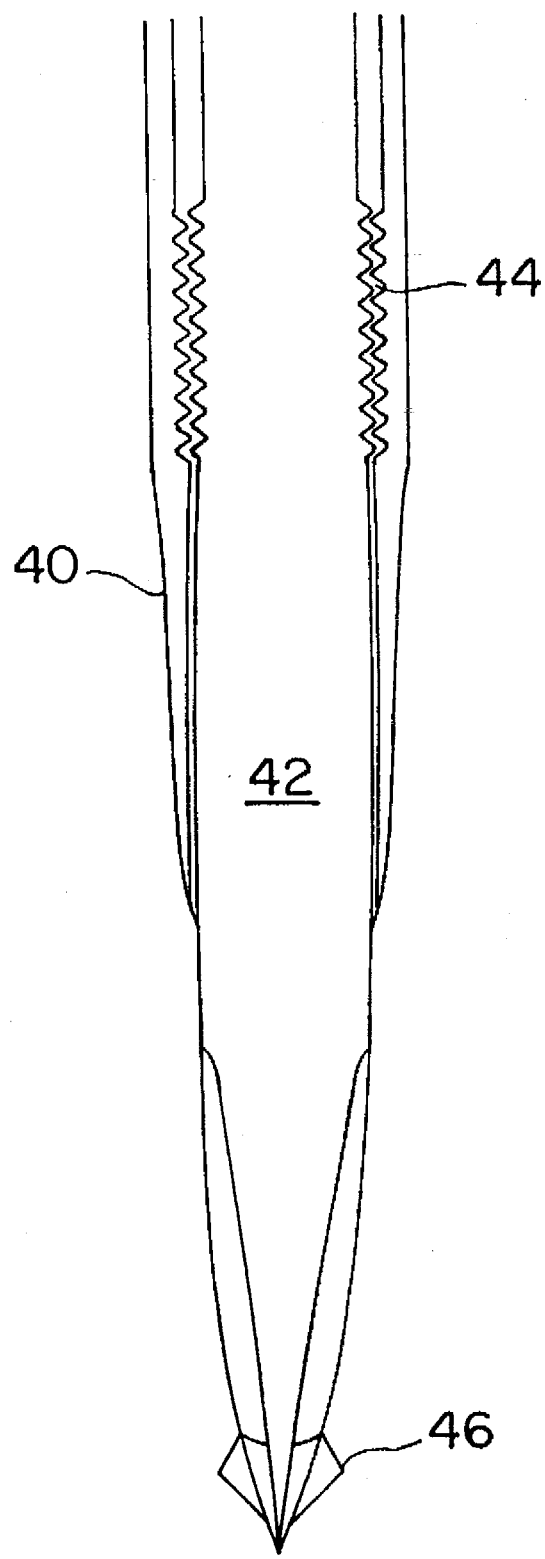
FIG. 2 illustrates a hollow outer needle and a solid inner needle adapted for insertion into the port shown in FIG. 1.

FIG. 2 depicts a needle system consisting of a hollow outer needle 40 and a solid inner needle 42. In the embodiment of FIG. 2, the two needles 40, 42 are connected by threaded interlock region 44, although any other suitable means of keeping the needle pair from separating can be used. The solid inner needle 42 facilitates puncturing through the skin of the patient without coring either skin tissue or the port's silicon septum. FIG. 2 also shows micro-cutting blades or fins 46, which can facilitate insertion.

The needle pair 40, 42 is inserted as a unit through silicon septum 22 into fluid storage reservoir 24 of port body 20. Outer needle 40 holds open a passageway through silicon septum 22 to reservoir 24, after which solid inner needle 42 is removed. Outer needle 40 extends completely through silicon septum 22, but need not continue through reservoir 24. Outer needle 40 may have markings to show the required insertion depth. Upon implantation of port body 20, the care provider may have marked the patient's skin with permanent ink to delineate the injection point providing best access to the subcutaneous port.

After removal of needle 42, a hollow inner needle 50 is inserted into the outer needle 40 so that it passes through the port's fluid storage reservoir 24. Inner needle 50 has a threaded tip 52, which in the embodiment shown is a set of male threads matching female-threaded basal receptacle 28. Tip 52 is screwed into port receptacle 28, to seat and securely interlock needle 50 to receptacle 28. Known torque-ratchet devices may be used to allow adequate torque to screw needle 50 into receptacle 28 without stripping the threads of tip 52 or crimping the body of needle 50.

Figure 3:
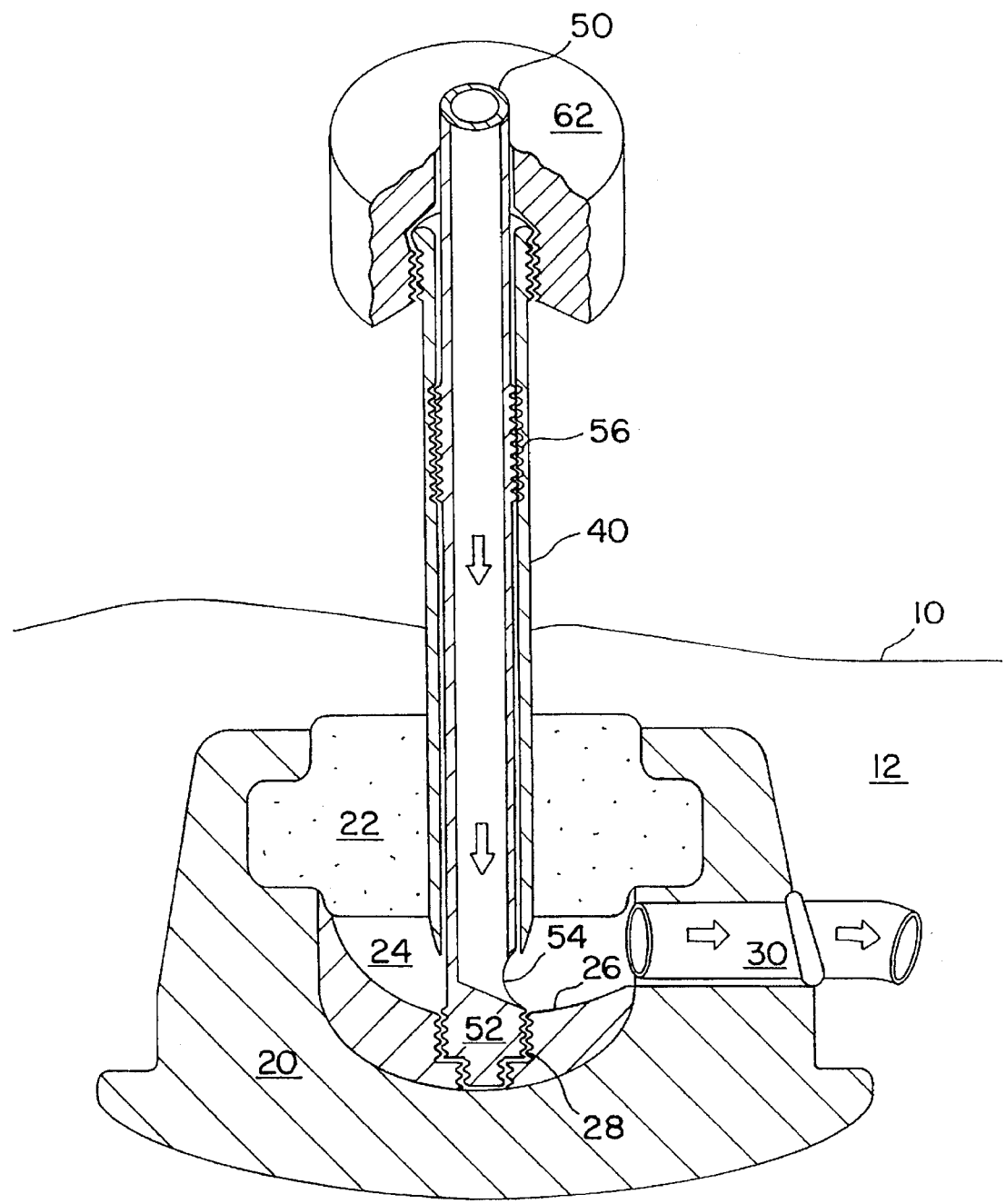
FIG. 3 shows the assembled needle and port structure in accordance with the invention, with a hollow inner needle in place and connected to an intravenous flow-line.

One or more apertures 54 are located on the side of needle 50, to allow fluid flow from the hollow interior of needle 50 into port reservoir 24, from where it passes through coupling 30 into the patient's vein, as shown by the arrows in FIG. 3.

Although the figure shows a single aperture 54, it is also possible to use a needle with two or several apertures on opposing sides of needle 50. Alternatively, needle 50 may contain a group of holes at different radial and lateral positions, which together match the flow area of the single aperture 54 shown. Also, if the structure of receptacle 28 permits, aperture 54 can alternatively comprise the hole at the end of needle 50 together with appropriate passageways through receptacle 28 to reservoir 24.

Inner needle 50 is connected to an intravenous flow-line 60 (shown in FIG. 1) using standard connection methods. Cap 62 (shown in FIGS. 1 and 3) may be screwed or placed onto outer needle 40, with either intravenous line 60 or inner needle 50 passing through a hole in the radial center of cap 62. Cap 62 hold the two needles together and connects inner needle 50 securely to line 60.

If desired, the two needles 40, 50 may be threadably connected to each other, as shown by interlocking thread area 56 in FIG. 3. Thread area 56 may be positioned to permit the care provider to confirm visually that inner needle 50 is adequately seated into the female-threaded receptacle 28 at the base of the port's reservoir 24.

The meshing male and female threading of the needles may be reversed from what is shown in the drawings, if desired.

In whichever embodiment, the spacings between the interlocking needle threads are selected to facilitate precise depth of placement of needle aperture 54 in the port's fluid reservoir 24, and precise placement in female-threaded receptacle 28.

It is preferred to use a system in which the total width of the threaded intervals—including the interval connecting 52 and 28 and, if present, thread area 56—is narrow, to minimize friction between body 20 and needle 50 when needle 50 is installed. Otherwise, such friction might tend to twist body 20, which could put unnecessary pressure on the patient's tissues. The interval at the end of needle 50, that is, the connection between 52 and 28, is particularly important, because it is the most distant from the point at which the needle is twisted. Thus, although the figures show threads that make several turns around needle 50, for the sake of clear depiction of the thread areas, in actual practice the threaded areas would preferably require fewer turns for complete insertion or at least fewer threads on one side of the interlocking halves. For example, it would be advantageous to use an interlock system in which a series of threads, much like that shown in the figures, is present on needle 50, but in which that series of threads fits into a receptacle 28 that includes only a single turn of thread or a series of spaced-apart thread segments or protruding flanges spaced so as approximate a turn of thread and to mate with the male threads of needle 50.

In some embodiments, it is advantageous to use an interlocking system that dispenses with thread area 56 and instead relies only on cap 62 to secure the needle pair together.

Although the drawings show threads of the sort used in a nut and bolt, the references to "threads" or "threading" herein can also include such suitable substitute rotatable engagement mechanism or other known substitutes. For example only, the term "threading" may refer to a pin and groove mechanism, in which one or more protruding pins fit into the top of L-shaped grooves in a receiving sleeve or base, are rotated after insertion, and are held by a notch-like or expanded area at the terminal end of the groove. Any other securing system known in the hardware or medical apparatus arts may also be substituted for the nut-and-bolt threads shown.

After an infusion is completed, the hollow needle pair is typically removed, and the port remains in the subcutaneous position until needed for the next cycle of chemotherapy, after which the above-described process is repeated.

Figure 4:
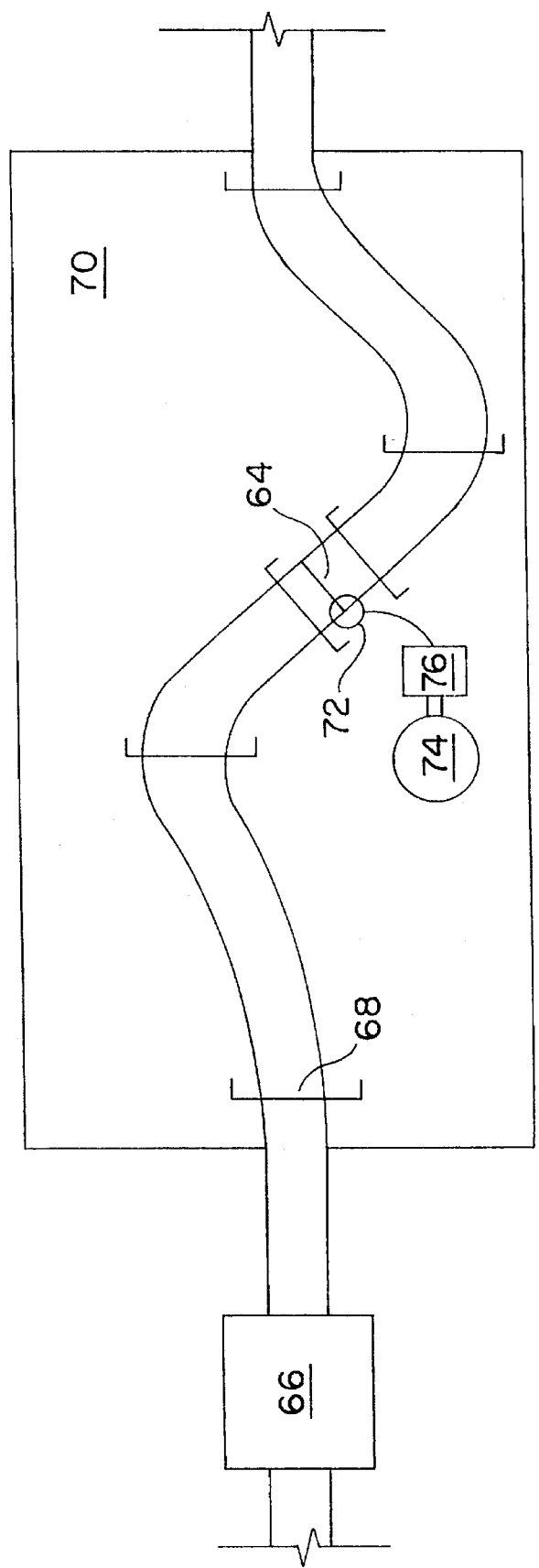
FIG. 4 shows a breakaway system along the flow-line to prevent needle displacement and resulting fluid discharge.

A weak point 64 in the intravenous flow-line 60 is shown in FIG. 4, whereby excessive tension, such as due to inadvertent patient movement or pulling of the flow-line, results in separation of the flow-line at point 64 instead of needle displacement. One-way flow ball valves like valve 66 can also be incorporated in the line, on either side of the weak point 64, to prevent blood or medicine seepage in the event that flow-line separation occurs during sleep or without the knowledge of the patient or care-giver. In the embodiment shown in FIG. 4, binding clips 68 (only some of which are shown in the figure) loosely couple flow-line 60 to card 70. At weak point 64, the two cut ends of flow-line 60 are opposed to each other and secured with tape or another leak-resistant method.

Clips 68 are made of a material or fastened to card 70 in a way that a predefined force, less than that necessary to pull out the needle or the port, will detach line 60 from between clips 68 and card 70. When a force above the predefined limit is applied, line 60 will separate at weak point 64, preventing damage to the port system. In the embodiment illustrated in FIG. 4, separation of line 60 at point 64 will also cause a change in pressure, forcing ball valve 66 to seal, thereby preventing backflow of medicine and blood from the port.

Alternatively or additionally, sensor 72, such as a wire loop circuit embodied in the tearable tape covering weak point 64, can detect separation, and signal device 74, such as a beeper secured to card 70 and powered by battery cell 76, can audibly inform the patient and caregivers of the partial or complete separation of the ends of line 60 held together at weak point 64. Such a system can help prevent or reduce the probability of infection, undetected loss of potentially expensive medicine, or contamination of medicine through exposure to air.

A simpler alternative to the system shown in FIG. 4 comprising card 70 and clips 68 can include a sleeve (not shown) covering and loosely fitted around the two opposed ends of line 60 at weak point 64 and containing on its inside a weak adhesive. The adhesive material and the sleeve, in combination, should be air-tight. If excessive force pulls on line 60, however, the adhesive will break, allowing one end or the other of line 60 to pull out of the sleeve, before the force is great enough to damage the seating of the needle or the port. The sleeve is preferably transparent, to permit the observation of any leaks of liquid medicine, such as by observing air bubbles passing between the sleeve and line 60.

Although the invention has been described with reference to specific embodiments, many modifications and variations of such embodiments can be made without departing from the innovative concepts disclosed.

Thus, it is understood by those skilled in the art that alternative forms and embodiments of the invention can be devised without departing from its spirit and scope. The foregoing and all other such modifications and variations are intended to be included within the spirit and scope of the appended claims.

We claim:

1. A subcutaneous venous access port apparatus for intravenous drug therapy comprising:

(a) a port enclosing an interior reservoir that is coupled to a catheter extending from the reservoir outside the port;

(b) a threaded receptacle on an interior surface of the reservoir;

(c) a hollow outer needle extending through the port to the interior reservoir; and (d) a hollow inner needle having threading configured to interlock with the threaded receptacle, and having at least one aperture extending from the hollow interior of the inner needle to the reservoir when the threads of the inner needle are interlocked with the threaded receptacle.

2. The apparatus of claim 1 wherein the reservoir has a concave surface surrounding the receptacle.

3. The apparatus of claim 1 wherein the port comprises a base and a self-sealing silicon septum, which are fitted together to enclose an interior reservoir, wherein the base supports the concave surface, and wherein the hollow outer needle extends through the septum.

4. The apparatus of claim 1 wherein the receptacle has female threading and the hollow inner needle has male threading substantially adjacent to the end of the inner needle on the interior of the port.

5. The apparatus of claim 4 wherein the female threading consists of approximately a single turn of screw threads.

6. The apparatus of claim 1 wherein the at least one aperture comprises a plurality of holes extending radially around a limited-length section of the hollow inner needle.

7. The apparatus of claim 1 wherein the outer needle further has a smooth exterior and internal threads, and wherein the inner needle has threads on its outer surface that interlock with the internal threads of the outer needle.

8. The apparatus of claim 1 further comprising a cap securing together the exterior ends of the outer needle and the inner needle and having a hole positioned to permit fluid flow into the inner needle through the cap.

9. The apparatus of claim 8 wherein the end of the inner needle passes through the hole in the cap.

10. The apparatus of claim 1 further comprising a flexible fluid flow-line coupled to the hollow inner needle, and further comprising a break-away section located along the fluid flow-line.

11. A subcutaneous venous access port system for intravenous drug therapy comprising:

(a) a port comprised of a base and a self-sealing silicon septum, which are fitted together to enclose an interior reservoir, wherein the base has a concave surface abutting the interior reservoir, and further comprising a hollow catheter coupled to the port so as to allow fluid to pass from the reservoir through the hollow catheter;

(b) a female-threaded receptacle on the center of the concave interior surface of the base;

(c) a hollow outer needle having internal threading;

(d) a first inner needle that is solid and has (i) external threading fitting the threading of the outer needle and (ii) a pointed end; and (e) a second inner needle that is hollow and has (i) first external threading fitting the threading of the outer needle, (ii) second external male threading substantially adjacent to the end of the second inner needle and configured to interlock with the female-threaded receptacle, and (iii) at least one aperture extending out of the hollow second inner needle between the first and second external threading;

(f) wherein the aperture is positioned to permit fluid to pass from the hollow interior of the second inner needle to the reservoir when (i) the outer needle extends through the silicon septum to the interior reservoir, (ii) the second inner needle extends entirely through the hollow outer needle, (iii) the end of the second inner needle outside the port is coupled to a source of fluid, (iv) the first threading of the second inner needle is fitted with the threading of the outer needle, and (v) the second threading adjacent to the end of the second inner needle inside the port is interlocked with the threaded receptacle.

12. The apparatus of claim 11 wherein the first inner needle further has a plurality of fins adjacent to the pointed end.

13. The apparatus of claim 11 further comprising:

(a) a flexible fluid flow line coupled to the hollow second inner needle;

(b) a break-away section located along the fluid flow-line; and (c) a ball valve along the flow-line adjacent to the break-away section on the side towards the second inner needle.

14. The apparatus of claim 13 further comprising a cap fitting over the exterior end of the hollow outer needle, and wherein the cap and outer needle are configured to permit secure attachment of the hollow second inner needle to the fluid flow-line through the cap.

15. A method of using a subcutaneous venous access port system for intravenous drug therapy comprising:

(a) implanting below the skin of a patient a port comprised of a base and a self-sealing silicon septum that are fitted together to enclose an interior reservoir, and a threaded receptacle on an interior surface of the base;

(b) coupling the reservoir to a hollow catheter surgically implanted into a vein of the patient;

(c) thereafter piercing the skin and the septum with, and extending into the reservoir, a unit substantially consisting of a hollow outer needle and a solid, pointed inner needle;

(d) thereafter removing the solid inner needle while leaving the hollow outer needle in place;

(e) thereafter placing entirely through the hollow outer needle a two-ended hollow inner needle that has (i) external threads substantially adjacent to a first end of the hollow inner needle, and (ii) at least one aperture extending out of the hollow inner needle between the two ends;

(f) thereafter interlocking the threads adjacent to the first end of the hollow inner needle with the threaded receptacle;

(g) coupling a source of fluid to the second end of the hollow inner needle; and (h) thereafter causing fluid to flow from the source, through the hollow inner needle, out of the aperture, and into the reservoir, and to flow from the reservoir, through the catheter, and into the vein.

16. The method of claim 15 wherein the base has a concave surface abutting the interior reservoir, and wherein the threaded receptacle is on the concave interior surface.

17. The method of claim 16 wherein the receptacle is female-threaded and the hollow inner needle has male threads at the first end.

18. The method of claim 15 wherein the hollow inner needle has further external threads fitting internal threads of the hollow outer needle, and wherein (e) comprises screwing the hollow inner needle into the hollow outer needle.

19. The method of claim 18 wherein the solid inner needle has external threads fitting the internal threads of the hollow outer needle, further comprising assembling the unit by screwing the solid inner needle into the hollow outer needle, and wherein (d) comprises unscrewing the solid inner needle from the hollow outer needle.

20. The method of claim 15 further comprising thereafter ceasing the flow of fluid and removing the hollow inner needle and the hollow outer needle, while leaving the port and catheter in place in the patient, and wherein removing the needles causes the septum to self-seal the hole previously held open by the outer needle.

* * * * *